(12) United States Patent
Mattar Neto et al.

(10) Patent No.: US 6,935,339 B2
(45) Date of Patent: Aug. 30, 2005

(54) SECRETION SUCTIONING DEVICE AND KIT FOR INTUBATED PATIENTS

(76) Inventors: Joao Augusto Mattar Neto, Av. dos Eucaliptos, 113 - apto 132, Sao Paulo - SP (BR), 04534-050; Danilo Augusto Calixto Besser, Rua Inhambu, 763 - apto 121, Sao Paulo - SP (BR)

( * ) Notice: Subject to any disclaimer, the term of this patent is extended or adjusted under 35 U.S.C. 154(b) by 10 days.

(21) Appl. No.: 09/838,863

(22) Filed: Apr. 20, 2001

(65) Prior Publication Data

US 2001/0029953 A1 Oct. 18, 2001

Related U.S. Application Data

(63) Continuation of application No. PCT/BR99/00084, filed on Oct. 13, 1999.

(30) Foreign Application Priority Data

Oct. 23, 1998 (BR) .............................................. 9804529
Oct. 13, 1999 (BR) .............................. PCT/BR99/00084

(51) Int. Cl.[7] ........................................... A61M 16/00
(52) U.S. Cl. .................................. 128/207.16; 128/912
(58) Field of Search ....................... 128/200.26, 207.16, 128/912, 202.27, 205.12, 205.24, 207.14

(56) References Cited

U.S. PATENT DOCUMENTS

| 3,902,500 | A | | 9/1975 | Dryden |
| 3,991,762 | A | | 11/1976 | Radford |
| 4,351,328 | A | | 9/1982 | Bodai |
| 4,569,344 | A | | 2/1986 | Palmer |
| 4,638,539 | A | * | 1/1987 | Palmer ...................... 29/157 R |
| 4,696,296 | A | | 9/1987 | Palmer |
| 4,805,611 | A | | 2/1989 | Hodgkins |
| 4,825,859 | A | | 5/1989 | Lambert |
| 4,834,726 | A | | 5/1989 | Lambert |

(Continued)

FOREIGN PATENT DOCUMENTS

| BR | PI 9804529-6 A | * | 4/2000 | ............ 128/207.14 |
| GB | 1174397 | | 12/1969 | |

OTHER PUBLICATIONS

Carlon et al., "Evaluation Of A Closed–Tracheal System," Critical Care Medicine, 1987, vol. 15, pp. 522–525.

Clark et al., "Effecs Of Endotracheal Suctioning On Mixed Venous Saturation And Heart Rate In Critically Ill Adults," Heart & Lung, 1990, vol. 19, pp. 522–557.

(Continued)

Primary Examiner—Aaron J. Lewis
(74) Attorney, Agent, or Firm—Hughes Hubbard & Reed LLP; Ronald Abramson; Douglas D. Zhang (57) ABSTRACT

This invention is a secretion, a suction device, and kit for intubated or tracheostomized patients including a suction valve (1) having a body (2) with a chamber (3) where a selective obstruction device (4) is assembled. The device further includes a spherical valve (45) which selectively opens or closes a passage for a probe (25) through a patient/ventilator connection (56). The kit allows for the correct positioning of the suction device, including a plastic sheathing (65), and a tube for disposal of the suction device.

22 Claims, 9 Drawing Sheets

U.S. PATENT DOCUMENTS

| | | |
|---|---|---|
| 4,836,199 A | 6/1989 | Palmer |
| 4,838,255 A | 6/1989 | Lambert |
| 4,846,167 A * | 7/1989 | Tibbals ................. 128/202.27 |
| 4,850,350 A | 7/1989 | Jackson |
| 4,872,579 A * | 10/1989 | Palmer ................. 128/205.19 |
| 4,938,199 A | 7/1990 | Sato et al. |
| 4,938,741 A | 7/1990 | Lambert |
| 4,967,743 A | 11/1990 | Lambert |
| 4,981,466 A | 1/1991 | Lumbert |
| 5,025,806 A | 6/1991 | Palmer et al. |
| 5,029,580 A | 7/1991 | Radford et al. |
| 5,065,754 A | 11/1991 | Jensen |
| 5,073,164 A | 12/1991 | Hollister et al. |
| 5,083,561 A | 1/1992 | Russo |
| 5,088,486 A | 2/1992 | Jinotti |
| 5,107,829 A | 4/1992 | Lambert |
| 5,125,893 A | 6/1992 | Dryden |
| 5,133,345 A | 7/1992 | Lambert |
| 5,134,996 A | 8/1992 | Bell |
| 5,139,018 A * | 8/1992 | Brodsky et al. ....... 128/207.14 |
| 5,140,983 A | 8/1992 | Jinotti |
| 5,176,415 A * | 1/1993 | Choksi ....................... 285/331 |
| 5,207,641 A | 5/1993 | Allton |
| 5,220,916 A | 6/1993 | Russo |
| 5,255,676 A | 10/1993 | Russo |
| 5,269,756 A | 12/1993 | Dryden |
| 5,279,549 A | 1/1994 | Ranford |
| 5,309,902 A * | 5/1994 | Kee et al. .............. 128/202.27 |
| 5,325,851 A | 7/1994 | Reynolds et al. |
| 5,335,655 A * | 8/1994 | Kee ....................... 128/207.16 |
| 5,336,192 A * | 8/1994 | Palestrant .................... 604/167 |
| 5,337,780 A | 8/1994 | Kee |
| 5,354,267 A | 10/1994 | Niermann et al. |
| 5,368,017 A * | 11/1994 | Sorenson et al. ...... 128/200.26 |
| 5,377,672 A * | 1/1995 | Kee ....................... 128/207.16 |
| 5,445,141 A | 8/1995 | Kee et al. |
| 5,449,348 A | 9/1995 | Dryden |
| 5,460,613 A | 10/1995 | Ulrich et al. |
| 5,490,503 A | 2/1996 | Hollister |
| 5,579,762 A * | 12/1996 | Lee ....................... 128/207.14 |
| 5,582,161 A * | 12/1996 | Kee ....................... 128/200.26 |
| 5,582,165 A | 12/1996 | Bryan et al. |
| 5,598,840 A | 2/1997 | Lund et al. |
| 5,611,336 A * | 3/1997 | Page et al. ............. 128/207.16 |
| 5,642,726 A | 7/1997 | Owens et al. |
| 5,645,048 A | 7/1997 | Brodsky et al. |
| 5,664,564 A * | 9/1997 | Palmer ................. 128/205.19 |
| 5,715,815 A | 2/1998 | Lorenzen et al. |
| 5,730,123 A * | 3/1998 | Lorenzen et al. ...... 128/207.14 |
| 5,735,271 A * | 4/1998 | Lorenzen et al. ...... 128/207.16 |
| 5,738,091 A * | 4/1998 | Kee et al. .............. 128/205.12 |
| 5,746,199 A * | 5/1998 | Bayron et al. ......... 128/205.24 |
| 5,779,687 A * | 7/1998 | Bell et al. .................... 604/265 |
| 5,957,898 A * | 9/1999 | Jepson et al. ............... 604/256 |
| 6,070,582 A * | 6/2000 | Kee ....................... 128/207.16 |

OTHER PUBLICATIONS

Czarnik et al., "Differential Effects Of Continuous Versus Intermittent Suction On Tracheal Tissue," Heart & Lung, 1991, vol. 20, pp. 144–151.

Deppe et al., "Incidence Of Colonization, Nosocomial Pneumonia, And Mortality In Critically Ill Patients Using a Trach Care Closed–Suctioning System Versus An Open– Suction System: Prospective, Randomized Study," Critical Care Medicine, 1990, vol. 18, pp. 1389–1393.

Johnson et al., "Closed Versus Open Endotracheal Suctioning: Cost And Physiologics Consequences," Critical Care Medicine, 1994, vol. 22, pp. 658–666.

Mattar et al., "A Clinical Comparsion Between Cardiac Output Measured By Thermodilution Technique And Noninvasive Thoracic Electrical Bioimpedance," Acute Care, 1986, vol. 12, pp. 58–60.

Mattar et al., "The Effects On Oxygen Transport With Varying Respiratory Flow Waveforms In Critically Ill Patients," Critical Care Medicine, 1997, vol. 25 (Suppl), p. A36.

Mattar et al., "Sistolic And Diastolic Time Intervals In Critically Ill Patients," Critical Care Medicine, 1991, vol. 19, pp. 1392–1398.

Mattar, "Noninvasive Cardiac Output Determination By Thoracic Electrical Bioimpedance," Intensive & Critical Care Digest, 1988, vol. 7, pp. 14–18.

Raymond, "Normal Saline Instillation Before Suctioning Helpful Or Harmful: A View Of the Literature," American Journal Of Critical Care, Jul. 1995, vol. 4, pp. 267–271.

Ritz et al., "Contamination Of A Multiple–Use Suctioning Catheter In A Closed–Circuit System Compared To Contamination Of A Disposable, Single Use Single Suction Catheter," Respiratory Care Nov. 1986, vol. 31, No. 11, pp. 1086–1091.

Cobley et al., "Environmental Contamination During Tracheal Suction," Anaesthesia, 1991, vol. 46, pp. 957–961.

Depew et al.. "Open Versus Closed Endotracheal Suctioning: A Cost Comparison," Critical Care Nurse, Feb. 1994, pp. 94–100.

Hess et al., "Care of the Ventilator Circuit and Its Relation to Ventilator–Associated Pneumonia," Respiratory Care, Sep. 2003, vol. 48, No. 9, pp. 869–879.

* cited by examiner

SECRETION SUCTIONING DEVICE AND KIT FOR INTUBATED PATIENTS

This application is a continuation of and claims priority to a prior-filed international application designating the United States of America, Application No. PCT/BR99/00084, filed on Oct. 13, 1999, which in turn claims priority to a Brazilian patent application, Application No. 9804529-6, filed Oct. 23, 1998.

This invention relates to a secretion suctioning device for intubated or tracheostomized patients, as well as to a secretion suctioning kit for intubated or tracheostomized patients, maintaining mechanical ventilation. The device, part of said kit, contains a suctioning valve, a sealing/instillation set, a spherical connection set (including a connection for the patient/ventilator tube), and a packaging that includes a plastic sheathing and a connector for disposal of the material.

Such invention relates to probes or catheters for tracheal suctioning, more specifically, the mechanical ventilation of a patient's respiratory system and the suctioning of the fluids accumulated in the patient's trachea or bronchi.

Particularly, this invention relates to a new apparatus (related method) to jointly maintain the ventilation, aspirate secretions from and instillate solutions into the patient's respiratory system, and wash the catheter, with no risks to the patient.

This application takes into consideration the following documents: U.S. Pat. No. 1,174,397 dated December 1969—United Kingdom 128/351; U.S. Pat. No. 3,902,500 dated September 1975—Dryden 604/171X;—U.S. Pat. No. 3,991,762 dated November 1976—Radford 604/119; U.S. Pat. No. 4,351,328 dated September 1982—Bodai 128/202.16; U.S. Pat. No. 4,569,344 dated February 1986—Palmer 128/207.16; U.S. Pat. No. 4,638,539 dated January 1987—Palmer 128/207.16; U.S. Pat. No. 4,696,296 dated September 1987—Palmer 128/207.16; U.S. Pat. No. 4,805,611 dated February 1989—Hodgkins 128/207.14; U.S. Pat. No. 4,825,859 dated May 1989—Lambert 128/207.16; U.S. Pat. No. 4,834,726 dated May 1989—Lambert 604/281; U.S. Pat. No. 4,836,199 dated June 1989—Palmer 128/207.16; U.S. Pat. No. 4,838,255 dated June 1989—Lambert 128/207.16; U.S. Pat. No. 4,850,350 dated July 1989—Jackson 128/207.16; U.S. Pat. No. 4,872,579 dated October 1989—Palmer 128/207.16; U.S. Pat. Nos. 4,938,199, 4,938,741 dated July 1990—Lambert 604/19; U.S. Pat. No. 4,967,743 dated November 1990—Lambert 128/207.16; U.S. Pat. No. 4,981,466 dated January 1991—Lambert 604/19; U.S. Pat. No. 5,025,806 dated June 1991—Palmer et al. 128/207.14; U.S. Pat. No. 5,029,580 dated July 1991—Radford et al. 128/207.14; U.S. Pat. No. 5,065,754 dated November 1991—Jansen 128/200.26; U.S. Pat. No. 5,073,164 dated December 1991—Hollister 604/43; U.S. Pat. Nos. 5,080,646; 5,083,561 dated January 1992—Russo 128/207.16; U.S. Pat. No. 5,088,486 dated February 1992—Jinotti 128/207.14; U.S. Pat. No. 5,107,829 dated April 1992—Lambert 128/202.16; U.S. Pat. No. 5,125,893 dated June 1992—Dryden 604/54; U.S. Pat. No. 5,133,345 dated July 1992—Lambert 604/171; U.S. Pat. No. 5,134,996 dated August 1992—Bell 128/207.14; U.S. Pat. No. 5,139,018 dated August 1992—Brodsky et al. 128/207.14; U.S. Pat. No. 5,140,983 dated August 1992—Jinotti 128/207.14; U.S. Pat. No. 5,220,916 dated June 1993—Russo 128/207.16; U.S. Pat. No. 5,255,676 dated October 1993—Russo 128/207.14; U.S. Pat. No. 5,269,756 dated December 1993—Dryden 604/54; U.S. Pat. No. 5,279,549 dated January 1994—Ranford 604/34; U.S. Pat. No. 5,325,851 dated July 1994—Raynolds et al. 128/204.16; U.S. Pat. No. 5,337,780 dated August 1994—Kee 137/381; U.S. Pat. No. 5,354,267 dated October 1994—Niermann et al. 604/32; U.S. Pat. No. 5,368,017 dated November 1994—Sorenson et al. 128/200.26; U.S. Pat. No. 5,445,141 dated August 1995—Kee et al. 128/203.12; U.S. Pat. No. 5,449,348 dated September 1995—Dryden 604/71; U.S. Pat. No. 5,460,613 dated October 1995—Ulrich et al. 604/118; U.S. Pat. No. 5,490,503 dated February 1996—Hollister 128/205.12; U.S. Pat. No. 5,582,165 dated December 1996—Bryan et al. 128/207.14; U.S. Pat. No. 5,598,840 dated February 1997—Iund et al. 128/207.14; U.S. Pat. No. 5,642,276 dated July 1997—Oewns et al. 128/200.26; U.S. Pat. No. 5,645,048 dated July 1997—Brodsky et al. 128/202.27; U.S. Pat. No. 5,715,815 dated February 1998—Lorenzen et al 128/207.14; and the following scientific publications: 1. Carlon G C, Fox S J, Ackerman N J. "Evaluation of a Closed-tracheal system." Crit Care Med 1987; 15:522–525; 2. Clark A P, Winslow E H, Tyler D O, et al. "Effects of Endotracheal Suctioning on Mixed Venous Saturation and Heart Rate in Critically Ill Adults." Heart Lung 1990; 19:522–557; 3. Cobley M, Atkins M, Jones P L. "Environmental Contamination During Tracheal Suction." Anaesthesia, 1991, volume 46, pp. 957–961; 4. Czarnik R E, Stone K S, Everhart C C, et al. "Differential Effects of Continuous Versus Intermittent Suction on Tracheal Tissue." Heart Lung 1991; 20: 144–151; 5. DePew C L, Moseley M J, Clark E G, Morales C C. "Open Versus Closed Endotracheal Suctioning: a Cost Comparison." Critical Care Nurse, Feb. 1994, pp. 94–100; 6. Deppe A S, Kelly W, Thol L L et al. "Incidence of Colonization, Nosocomial Pneumonia, and Mortality in Critically Ill Patients Using a Trach Care® Closed-suction System Versus and Open-suction System: Prospective, Randomized Study." Crit Care Med 1990; 18:1389–1393; 7. Grossi A S. "Closed Endotracheal Suction System for the Prevention of Hypoxemia." Rev Esc Enfermagem USP 1995; 29:1 26–33; 8. Johnson K L, Kearneu P A, Johnson S B, et al. "Closed Versus Open Endotracheal Suctioning: Cost and Physiologics Consequences." Crit Care Med 1994; 22:658–666; 9. Mattar J A, Baruzzi A C A, Diament D; et al. "A Clinical Comparison Between Cardiac Output Measured by Thermodilution Technique and Noninvasive Thoracic Electrical Bioimpedance." Acute Care 1986; 12:58–60; 10. Mattar J A, Bastos J T, Silva L A, et al. "The Effects on Oxygen Transport with Varying Respiratory Flow Waveforms in Critically Ill Patients." Crit Care Med 1997; 25(Suppl) A36; 11. Mattar J A, Shoemaker W C, Diament D, et al. "Sistolic and Diastolic Time Intervals in Critically Ill Patients." Crit Care Med 1991; 19: 1392–1398; 12. Mattar J A, Sproesser, Jr A J, Gomes M V. "A Comparative Study of Oxygen Transport Ruring Open and Closed Methods of Tracheal Suctioning." Int & Crit Care Dig 1992; 11:57–58; 13. Mattar J A. "Noninvasive Cardiac Output Determination by Thoracic Electrical Bioimpedance." Int & Crit Care Dig 1988; 7:14–18; 14. Raymond S J. "Normal Saline Instillation Before Suctioning Helpful or Harmful. A Review of the Literature." American Journal of Critical Care, July 1995, issue number 4, number 4, pp., 267–271; 15. Ritz R, Scott L R, Coyle M B, Pierson D J. "Contamination of a Multiple-use Suction Catheter in a Closed-circuit System Compared to Contamination of a Disposable, Single Use Single Suction Catheter." Respiratory Care, November 1986, volume 31, number 11. pp. 1086–1091.

As it is known by the medical professional area, the critically ill ICU (Intensive Care Unit) patient under mechanical ventilation has a physiologic balance that keeps him alive, and depends on an acceptable blood and tissue oxygenation level provided by the ventilatory support.

During the tracheal suctioning periods routinely performed in an intermittent manner, for the twenty-four hours of the day, an important blood oxygen desaturation may occur, which can lead to cardiac arrhythmias, low cardiac output, blood pressure variation, and other disturbances. Should this set of disturbances be analized in a suctioning episode, the transitory abnormal physiologic situation reverts itself when reinstalling the effective ventilation, without apparent permanent damage; however, considering that the patients under mechanical ventilation have a prolonged stay at the ICU, the accumulated sum of these shortages may be harmful and may have an influence on the survival time.

Furthermore, during the pulmonary secretion suctioning procedure, tube contamination may be caused where the catheter is to be introduced in the patient, the user as well may be contaminated with the secretion expelled from the patient's lung. Cobley et al., Deppe et al. and Ritz et al. discuss the environmental contamination issue, cross contamination, and other means of contamination during the tracheal suctioning.

One of the first proposed solutions in the past, in order to overcome these problems, was to sheath the catheter in a flexible glove, to prevent it from being touched. This apparatus is described by the English patent 1.174.397, from 1969, granted to the National Research Development Corporation. This apparatus, nevertheless constituting a breakthrough in the sterile handling of suctioning probes, did not resolve the problem of hypoxia, during and after the suctioning, among other problems that continued without solution.

Dryden, in 1975, obtained the North American patent under number 3.902.500, with an apparatus mentioned in almost all subsequent patents, related to simultaneous suctioning and ventilation. Dryden proposed the catheter sheathing the glove, be sealed from both sides. Beyond that, the oxygen could be introduced inside the glove, which would inflate, thus directing oxygen to the patient, through the compression of the glove. The patent also proposed an adapter which would allow a connection to a ventilator, thus allowing ventilation simultaneously with the suctioning procedure.

In 1976, Radford was granted the North American patent under number 3,991,762, that proposed a mechanism connected to the patient, which could operate for ventilation and suctioning, including a irrigation route, a medicine introduction route and a valve-like device to trigger the vacuum, among other innovations. This system, however, presented a series of problems, such as excessively expensive components, excessive weight over the endotracheal tube, possible inadequate aspiration, mechanical handling potentially harmful to the endotracheal tube, sheating impairment of the endotracheal probe, assembling and disassembling difficulties, possible expelling of the secretion to the atmosphere, etc.

Later, a series of patents were granted in the United States, especially to Darrel Palmer and Richard C. Lambert, having Ballard Medical Products as the holder, the most important being as following: U.S. Pat. Nos. 4,569,344; 4,638,539; 4,696,296; 4,825,859; 4,834,726; 4,836,199; 4,838,255; 4,872,579; 4,938,199; 4,938,741; 4,967,743; 4,981,466; 5,025,806; 5,080,646; and 5,133,345.

These patents intend to overcome the previous techniques' imperfections, comprising an apparatus (and a related method) that integrated in a single item the ventilating capacity to ventilate the patient and to aspirate fluids from his trachea and bronchi. It also looked to reduce traumas and risks for the patient, to avoid inadequate aspiration caused either by the patient himself or by the nurse or nurse's aid, and to avoid secretions from being expelled into the atmosphere during the periods when suctioning was not being performed. Furthermore, the inventions intended to be more feasible, from an economic point of view, than the previous ones.

From these and other patents, a product is currently marketed worldwide with the tradename "Trach Care", available in several models (adult and neonatal) and gauges: 05, 06, 08, 10, 12, 14, 16 and 18 "Fr", with details such as double lumen (for irrigation), "directional tip" (for selective suctioning of the bronchi), a special model for tracheostomized patients, and so on.

Another series of patents were also granted in the United States, having Smiths Industries Medical Systems as its holder, some of which are listed as follows: U.S. Pat. No. 5,073,164 (William H. Hollister);U.S. Pat. No. 5,134,996 (Craig J. Bell); U.S. Pat. No. 5,460,613 (Karl Ulrich and Thomas Devlin); and U.S. Pat. No. 5,490,503 (William J. Hollister).

Smiths Industrial Medical Systems introduced in the market the "Stericath", also presented in several gauges and models, currently marketed worldwide.

One, of the various intentions of these new inventions, was to solve the air opening within the catheter sheathing plastic glove problem, which led the glove to inflate, and made the subsequent use of the device more complicated.

From the Trach Care and Stericath products marketing, the tracheal closed suctioning system use became, little by little, routine in hospitals worldwide, starting in the 80's.

Simultaneously, in several comparative clinical trials between closed and open suctioning, the advantage of closed suctioning over the open one was demonstrated, including higher patient survival levels, which nowadays justifies the routine use of such method in substitution to the classic open suctioning.

After reviewing various essays on this subject, Mattar et al. (1986) had the opportunity to develop a nation wide study, involving three ICUs, including a total of 22 patients upon mechanical ventilation, aiming at the oxygen transport rate confirmation during the classic open suctioning ("OS") and sequentially, on the same patient, during the closed suctioning ("CS"). The group had already performed other studies, aproaching physiologic variables that, directly or indirectly were important as well to the global analysis of the results.

Some of the most important comparative studies on "OS" versus "CS" will be discussed below.

Carlton and his medical nursing staff from the Anaesthesia and Intensive Medicine Department of Memorial Sloan-Kettering Cancer Center (New York), studied in 1987 the benefits of "CS" in twenty patients, ventilated with the use of variable levels of final expiratory positive pressure ("FEPP"), which in "OS" is known to drop to zero. The measures performed before and after both suctioning types, performed sequentially, were: carbonic gas blood partial pressure ($PaCO_2$), oxygen arterial saturation ($SaO_2$), and oxygen pressure alveolus—arterial gradient (A-a $O_2$). It was statistically demonstrated that these oxygen rates lowered only in "OS", implying that the lowering in "FEPP" as one of those principally responsible for the reported variation. In "CS", since the "FEPP" levels are maintained, there was no significant lowering of these rates. The authors also mention as a potential advantage the prevention of secretion dissemination into the environment.

A broad study in Houston, Tex. hospitals, developed in clinical and surgery ICUs and coordinated by Deppe, comprised a total of 84 patients, studied concerning the nosocomial pneumonia incidences and, especially the survival rate. No differences were reported between "OS" and "OS" related to the pneumonia incidence, however, there was a distinct difference on the survival rate (studied up to 900 hours of hospital internment) with "CS".

During the same year (1990), another group formed by a nursing staff of 4 hospitals from Texas University (Austin) and Texas University (Arlington), developed a meticulous and well conducted study supported by the NIH—National Institute of Health, with the object of comparing "OS" and "CS", relating to the oxygen saturation in mixed venous blood from the pulmonary artery ($SvO_2$) and heart rate ("HR") in 189 patients. The main finding was the increase of "$SvO_2$" in "CS", while there was a lowering during the procedure in "OS", noticing also an advantageous persistency of supra-elevated values up to 2 minutes after the "CS" termination.

Statistically, there were no differences between the relationship of "HR" studied in both groups, and other important points were the preservation of the "FEPP" level and the same adjustment of the ventilator in "CS", while in "OS", in many cases, there was a loss of control of the adjustment prior to the ventilator disconnection to the "OS"'s procedure, and obviously, "FEPP" levels suppression (Clark et al).

Czarnit et al., from the Columbus Nursing Research Center, Ohio, studied the anatomicopathological changes in both "OS" and "CS" methods in 12 dogs, with special regards to the tracheal mucosa ulceration and necrosis at several levels, not describing significant differences in both groups studied. There is no reference to physiologic or hemodynamic data, and such experimental findings may not always be applied to the medical practice.

A more recent study (1994) by Johnson et al., in trauma units in Lexington, N.Y., comprised 35 patients with multiple traumas, divided into "OS" (16 patients) and "CS" (19 patients), with a total of 276 suctioning procedures (127 "OS" and 149 "CS"). The data studied before and after the procedures were: average arterial pressure ("AAP"), heart rate ("HR"), presence of arrhythmia, arterial and venous oxygen saturation ($SaO_2$ and $SvO_2$), nosocomial pneumonia incidence and daily patient procedure costs. The final results of the study show: I. Higher "AAP" in "OS"; II. Equal "HR", but persistent elevated "HR" 30 seconds after "OS"'s termination; III. Lower arrhythmia incidence in "CS"; IV. $PaO_2$ and $PvO_2$ lowering in "OS" and increase in "CS"; V. There were no differences between the pneumonia rates; VI. The operational cost of "OS" was USS 1,88/patient/day greater than in "CS", besides occupying higher nursing time than "OS".

In Mattar et al. (1992), the comparative study variable was the oxygen transport rate ("$O_2TR$") During the protocol elaboration, the authors profited from the previous experience with the cardiac rate ("CR") noninvasive monitoring method, joined to continuous "$SaO_2$" data through pulse oxymeter, and the hemoglobin dosage, usually present is such patients. Summarizing, that normal "$O_2TR$" is around 600 ml/$O_2$/min/$m^2$ of body surface and is estimated by the formula: "$O_2TR$"="CR" (L/min/$m^2$)×Hb(g/dL○×13,6 $SatO_2$(%)×10. The "$O_2TR$" values were selected at the suctioning beginning (B), termination (T), and the maximum (Mx) and Minimum (Mn) values were also estimated during the entire procedure. "OS" and "CS" were alternated and consequently applied to the same patient, and the results, as average values, are summarized below:

|  | (B) | (T) | (Mx) | (Mn) |
| --- | --- | --- | --- | --- |
| "$O_2TROS$" ml/min/m | 352 | 322 | 364 | 305 |
| "$O_2TRCS$" ml/min/m | 355 | 35 | 365 | 334 |

All the variables studied, with an influence on the survival rate of the critically ill patient under mechanical ventilation, may undergo changes, according to the suctioning procedure clinical status, especially relating to the cardiac cycle conditions and type of ventilation flow applied, as highlighted by Mattar (1991 and 1997).

In 1995, Grossi (USP Nursing School) published a review study on the practical aspects of the subject, proving that "CS" was more effective than "OS" in the maintenance of the $PaO_2$ in most of the patients studied.

Johnson et al. and Depew et al., among other studies identified in the technical literature, made a comparison of the cost/benefit relationship between open and closed suctioning systems, arriving to the conclusion that the closed suctioning happens to be less expensive than the open one.

This brief literature review is to show the scientific and financial acceptance of the use of tracheal suctioning through closed system procedures, comparing it to the now considered old fashioned open system.

Currently, a series of other products are marketed as Closed Tracheal Suctioning Systems, that are proposed to be better than those previously existing: Sherwood Medical Company; MedCare Medical Group (East Swansey, N.H., USA), under the name ACCS™ (Airway Catheter Cartridge System) Jinotti™; BLD Medical Products (Dallas, Tex., USA), under the name Neo-Link plus™; Mallinckrodt, under the name Hi-Care; Allegiance Healthcare Corporation (McGaw Park, Ill., USA), under the name Trach-Eze™; Hudson RCI, under the name Cath-Guide Closed Suction Catheter; Vital Signs Ind., under the name Iso-Cath™.

Several patents are also referenced in the beginning of this applcation concerning these products, or even related inventions, though not available in the market.

Some of the innovations proposed in these patents are: more comfortable apparatus for the patient, with a cost lower than the currently marketed; different valve systems to trigger the suctioning; systems totally closed during the catheter wash-out (which are opened solely during the passage of the catheter to perform the suctioning); instillation routes positioned in different parts of the system; spinning connections, and in elbow shape; etc.

Aiming at the invention hereby proposed, it is advisable to make comments on some patents mentioned herein.

The U.S. Pat. No. 4,805,611 was granted in 1989 to Harold M. Hodgkins. His main concern is with the suctioning valve position, in his appraisal, too distant from the patient, that can lead to inadequate aspiration. His proposal is to approximate the system connection valve to the patient, so that the introduction does not imply the moving of the valve and other parts of the system. Although interesting, this proposal presents problems, for instance, during the introduction of the catheter, which will be bent at all times, causing possible suctioning distress. The inadequate aspiration matter, in the patent hereby proposed, is overcome by the closed chamber and the visual indication for the operator, as well as the spherical set minimizes the moving effects of the set on the patient.

The U.S. Pat. No. 5,083,561, granted in 1992 to Ronald D. Russo, presents an interesting discussion on the suctioning valve structure different from the prior technique. In Russo's point of view, there is no need for a valve, likewise proposed in the previous inventions, but only a system positioned externally to the probe secretion flow for the vacuum, which triggers the vacuum. He proposes then a clamp system to trigger the vacuum and stop its flow, so that the secretion does not pass through its interior, thus avoiding the secretion accumulation within the valves, which, in Russo's opinion, would lead to the impaired functioning or even the valve suctioning capacity interruption. Russo's concern seems to be quite pertinent, but the proposal, however apparently feasible, presents enormous difficulties in its applicability, in terms of engineering.

This invention proposes an internal closure system to the suctioning valve, which prevents the secretion accumulation within the valves, thus avoiding the problems pointed out by Russo, in a simpler and more economic manner.

The U.S. Pat. No. 5,255,676, granted to Ronald D. Russo on Oct. 26, 1993 proposes, among other advantages, the use of an irrigation route in a diaphragm shape, which, besides being cheaper than the other means proposed by the copetitors, avoids the oxygen loss that occurs when the irrigation means are left open.

However, the diaphragm used as a substitute for the irrigation route presents some risks, for instance, the wearing of the material, handling difficulties with syringes or I.V. tubes, etc. The invention herein proposed suggests the maintenance of the irrigation route, because of the facility it presents regarding the I.V. tube or syringe handling, but reinforced by the use of an internal diaphragm to the irrigation route, in addition to the protection against oxygen loss through the closed chamber.

An interesting patent, granted to James F. Bryan and Blaine E. Black (U.S. Pat. No. 5,582,165) in 1996, proposes the invention of a catheter, sheatered in plastic, that can be connected to a vacuum source and to an endotracheal tube, making a closed system. The interesting point of the invention is that the plastic itself, used to protect the catheter (and the user) becomes plastic packaging for the catheter disposal after its use. For the very first time, as far as it is known, appears the concern, associated with the invention of a new model of Tracheal Suctioning Closed System, with the disposal of the system itself, taking into consideration the possible infection carriers that may be created by the material after its use. However, the invention appears to be very complex and not feasible in its assembly, and even in the catheter disposal. On the other hand, the invention herein discussed, concerns also the disposal, but proposes a safer and more feasible system than that of Bryan and Beck.

The U.S. Pat. No. 5,645,048 granted to David I. Brodsky and Harry O. Olsen in 1997 presents an innovation concerning the state of the prior technique. It presents the possibility of using as disposable only a central part of the kit, being able to be used for either the part connecting to the patient, or the part connecting to the vacuum. In addition to proposing a lowering in the cost, with the parts of the kit keeping for longer, the invention further proposes a connecting route between both ends of the central disposable part of the kit, so that the disposal of the material is more hygienic.

The use of only a part of the system as disposable showed to be an economic, feasible, and safe proposal, and it has been already used by some manufacturers. However, there is no appropriate indication for the user that the system is closed or open, which disqualifies the invention, since the system may stay open, disabling the closed chamber function. The invention herein proposed presents a series of innovations in this respect: a sphere as a separation between the disposable and fixed parts of the system; a color indicator (red and green) which allows the user to identify whether the system is closed or opened; an easy handling key, which allows the opening and the closure of the system, without keeping the user's hand busy during the suctioning procedure, and etc.

Raymond's et al. study proposes that the use of saline solution instillation be discontinued, because of the damages it may cause to the patients. Though we do not completely share Raymond's conclusion, as we could agree with the use of the instillation to liquefy the secretion to be suctioned, for instance, we believe that a closed system should not allow that the saline solutions used for the probe wash-out end up being aspirated by the patient. In the case of the currently marketed products, noted previously, it ends up being necessary to lift the patient's head during the probe wash-out procedure, to prevent the saline solution from going down the endotracheal tube, which, obviously, causes uncalculated damages to the patient's recovery, besides the distress caused to both the patient and the user. The proposal presented by this invention includes a sphere with color indicator, which closes the system with a visual indication and completely seals off the probe reflux for the patient, thus allowing the catheter wash-out without any contact whatsoever with the patient.

The concern with the disposal of the system, especially due to the high levels of hospital contamination that the scientific community tries to overcome, in global terms, has become essential for every medical product. Our proposal implies a series of inventions: a connector coupled to the kit packaging, which allows both system ends to be connected in its interior, thus avoiding the possibility of secretion being expelled after the connection; a plastic coupled to the kit packaging, in which the disposable part of the system should be inserted every twenty-four hours (and as well as the part that remains longer, at the time that it should be changed), and which will be closed and disposed of (thus preventing any type of contamination to be transmitted to the environment, users, patients, hospital waste collectors, etc).

U.S. Pat. No. 5,715,815, granted to Lorenzen et al., suggests a seal-shaped filter, to preserve the system sterilization. However, the invention seems to be insufficient, since the invention hereby proposed suggests a much more effective sealing system.

There is no concern, in all the inventions surveyed, regarding the air flow that goes from the ventilator to the patient. None of the proposals of the prior techniques status considers a physiologic air flow, by presenting sketches that have direct influence on the air pathway to the patient.

The proposed invention also concerned with this factor, proposing a sketch for the tube-ventilator connector, which allows a much more physiologic flow than the previous inventions.

As it is observed through the different parts that compose our proposal for a "CS" kit, there are several innovating possibilities that the previous devices that were considered state-of-the-art do not consider. In addition, such an invention proposes to be simpler and less expensive than the current technique.

It is expected that, with the routine implementation of the "CS" system hereby proposed, there are savings with regards the previous inventions (which creates consequences for the patients, to health care institutions, medical plans, etc.), greater ease in the system handling by the nurse, higher survival rates especially with patients under mechanical ventilation with prolonged stays in ICUs such as those with multiple traumas, respiratory infections, postoperative complications, neurologic disturbances, and other conditions.

Taking into consideration the description of the current technique, and the problems previously noted, this invention overcomes and/or relieves the above mentioned problems, and consists of an endotracheal secretion suctioning kit, maintaining the mechanical ventilation of the patient, allowing the probe wash-out in a manner that prevents the saline solution from passing to the patient, with a colored sphere indicating the opening and closure of the system, vacuum triggering anatomic valve, sealing system through a three-ring set, and accessory components for the safe disposal of the material after use. The kit, among other functions, allows savings through the disposal (after 24 hours) of the set for installation/sealing, keeping the valve and the sphere connection for longer; disposal with no contamination risks for the patient, users and all people who might handle the product as hospital waste; laminar air flow sent to the patient by the ventilator, which creates a more physiologic ventilation procedure; safe sealing and complete in several parts, protecting thus the patient, users and environment from possible contamination; handling facility for the users; accessory coupling possibility (such as filters, humidifiers, fixtures, secretion collection flasks, etc.), all essential during the suctioning procedure; visual identification for the users through colors, indicating whether the system is open or closed; prevention of secretion accumulation risks within the suctioning valve, through a sealing ring system; etc.

One of the objects of the invention is to provide a tracheal suctioning kit which maintains the mechanical ventilation of the patient, overcoming several problems found in the previous techniques.

Another object of this invention patent is to provide a closed system tracheal suctioning kit, containing a central disposable set each 24 hours, with visual marking for the user when the system is closed or open, thus avoiding the absorption of undesired saline solution by the patient, and avoiding the system from remaining inadvertently open, allowing endoscopy (or other) exams to be performed, keeping the patient ventilated without the need for completely disconnecting the kit, among other functions. The set consists of a colored sphere, with red and green colors, indicating whether the system is closed or open. The sphere has an easily adjustable selection key, which allows the user to open or close the system and then free his hand for other functions during the suctioning procedure. One of the parts of the set connects to the ventilator and to the patient, through a double swivel connection. The other part of the set connects to the sealing/instillation set. When the system is open, the probe passage through the sphere's interior is possible, in order to allow the suctioning. When the probe is returned to its initial position, the sphere is closed, thus isolating the probe and the patient's instillation route.

Another object of this invention is to provide a tracheal suctioning kit, maintaining the mechanical ventilation, with a suctioning triggering anatomic valve system, with total sealing of the system, thus avoiding the secretion accumulation which would eventually damage the functioning of said kit.

Another object of this invention is to provide a tracheal suctioning kit, maintaining the mechanical ventilation, with total sealing of the system, with a special three internal ring sealing system.

Another object of this invention is to provide a tracheal suctioning kit, maintaining the mechanical ventilation, which allows the effective and safe disposal of the material from the moment the kit (or part of it) is removed from the patient, until the moment it becomes hospital waste, thus avoiding several types of contamination (for the environment, the users, the patient himself, and all those who handle hospital waste, etc.). The sealing/instillation set should be disposed of every 24 hours. Each end should be inserted into a connector, which comes with the packaging, thus avoiding the secretion contained in the set from leaking and acting as an infection agent. The set, already protected by the disposable connector, should also be inserted into a special plastic sheating, which also accompanies the packaging of the kit, and avoids the contamination created by the material when it becomes hospital waste.

Another object of this invention is to provide a kit for tracheal suctioning maintaining the mechanical ventilation, with a design that allows a laminar air flow that proceeds from the ventilator to the patient, thus avoiding turbulences that eventually become harmful for the maintenance of the artificial respiration.

Another object of this invention is to provide a tracheal suctioning kit, maintaining the mechanical ventilation, which presents larger handling facility for the users. From the moment the spherical selecting key is handled, opening or closing the system, there is no need for the user to keep his hand busy with the said key, thus releasing said hand for any other necessary activity during the suctioning procedure or probe wash-out. The anatomic valve system allows greater ease in the vacuum triggering, also creating less fatigue for the system users.

Finally, another object of this invention is to provide a tracheal suctioning kit, which allows the maintenance of the mechanical ventilation, more economical than the prior inventions. The fact that only the sealing/instillation set is disposable, the facilities presented for the problem solving, presented by the previous inventions (but whose proposals were unfeasible, from an engineering point of view, or even extremely expensive), the simplicity of the proposed ideas, etc. make this invention more cost effective than those previous known.

Following, the device itself will be described in a detailed manner, regarding the sketches listed below, of which:

FIG. 7 illustrates a view that exemplifies, in a schematic manner, the possibility of disposal of the device hereby proposed, more specifically, the above mentioned FIG. 7 illustrates the refill disposal operation of such a device, which comprises its probe and respective protective sheathing of the set;

Pursuant to what the above listed figures illustrate, the secretion suctioning device comprises a suctioning valve 1, defined by a body 2, provided with a chamber 3, where a selective obstruction device 4 is assembled, formed by a pin 5, triggered by upper button 6, which acts against the action of a spring 7.

The chamber 3 is comprised of a channel selector 71, below pin 5, which is intended to be occupied by the lower rim 72 of said pin, this condition occurs with the heating of the suctioning valve 1.

The angle between the chamber 3 and the connection 11 causes the o-rings 8 to always be under a sealed condition, with valve 1 both under triggering or rest conditions.

Pin 5, as it was referred to, has two sealing 8 o-rings, assembled under ring necking 9, assembled upper and lower to a passage opening 10, through which the secretion passes, during the vacuum application moment.

The suctioning valve 1 operating systems determines that it may be conveniently locked, which prevents pin 5 from being inadvertently triggered, accidentally communicating the vacuum in this device.

Figure 3:
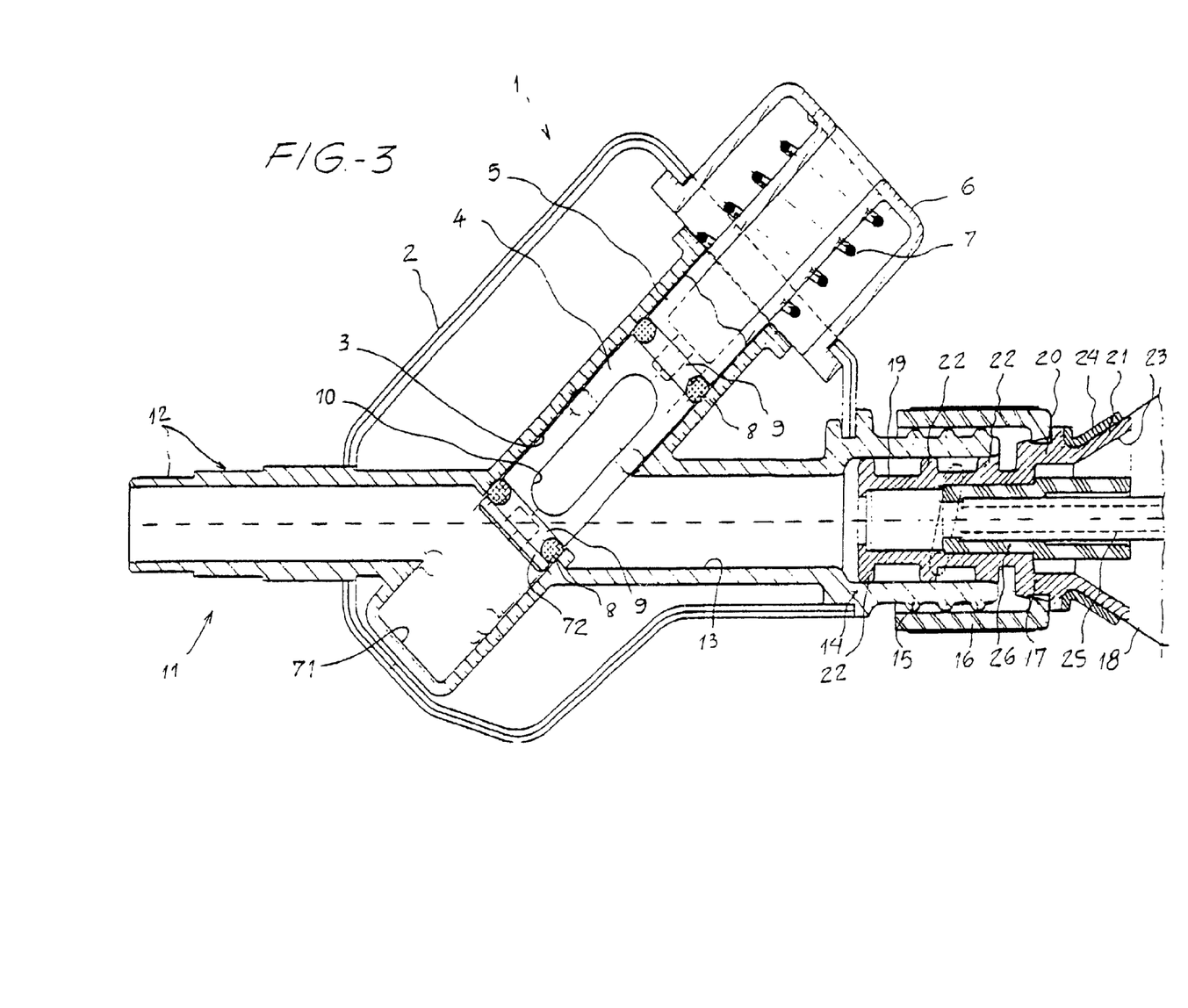
FIG. 3 illustrates an enlarged detail taken from FIG. 2, which demonstrates the suction valve.

FIG. 3 illustrates a condition in which said pin is found to be completely retracted, fact that determines the misalignment of its passage opening 10.

By this, for the vacuum to be communicated with the suctioning valve 1, pin 5 must be turned by 90 degrees, thus leaving its locked condition, which is determined according to the upper button 6, along body 2 of valve 1.

Body 2 of the suctioning valve is provided with a connection that acts for the vacuum line coupling (not illustrated), which is used to produce the secretion withdrawal from inside the device, said connection 11 incorporates a progressive staggering 12, a fact which allows the use of several vacuum line diameters.

Connection 11, as demonstrated on FIG. 3, crosses chamber 3 and is aligned with an internal channel 13, which crosses body 2 of suctioning valve 1.

Body 2 is further provided with an rim connection 14, provided externally with a thread 15, to which is threaded a binding element 16, used to produce the coupling of a interconnection component 17, used to produce the plastic sheathing 18.

The interconnection component 17, basically comprises three regions defined as anterior 19, median 20 and posterior 21, each one with a specific object. The anterior region 19, is provided with ring ribs 22, preferably in three, which act as a means of sealing, regarding the internal wall of the rim connection 14. The median region 20 incorporates an outlining external wall, with an adequate profile to the tight connection with the binding element 16, making possible the interconnection component 17 to be axially dislocated, thus producing its fixation along body 2 of the suctioning valve 1. The posterior region 21 incorporates a trunk configuration ending 23, which acts as an adequate place for the rim plastic sheathing 18 positioning, being said ending 23 the place for the retention ring 24 positioning, which guarantees the sealing and tight positioning of the already mentioned sheathing 18.

The interconnecting component 17 receives internally the ending of a probe 25, which depending on its gauge may be assembled or not on a tie rod 26, which has the object of allowing the use of probes 25 with more than a measure of external diameter.

For this reason, the tie rod 26 is provided with a standard external diameter, to allow its introduction into the interconnecting component 17, besides being also provided with two measure of internal diameter to receive the probe 25.

Figure 1:
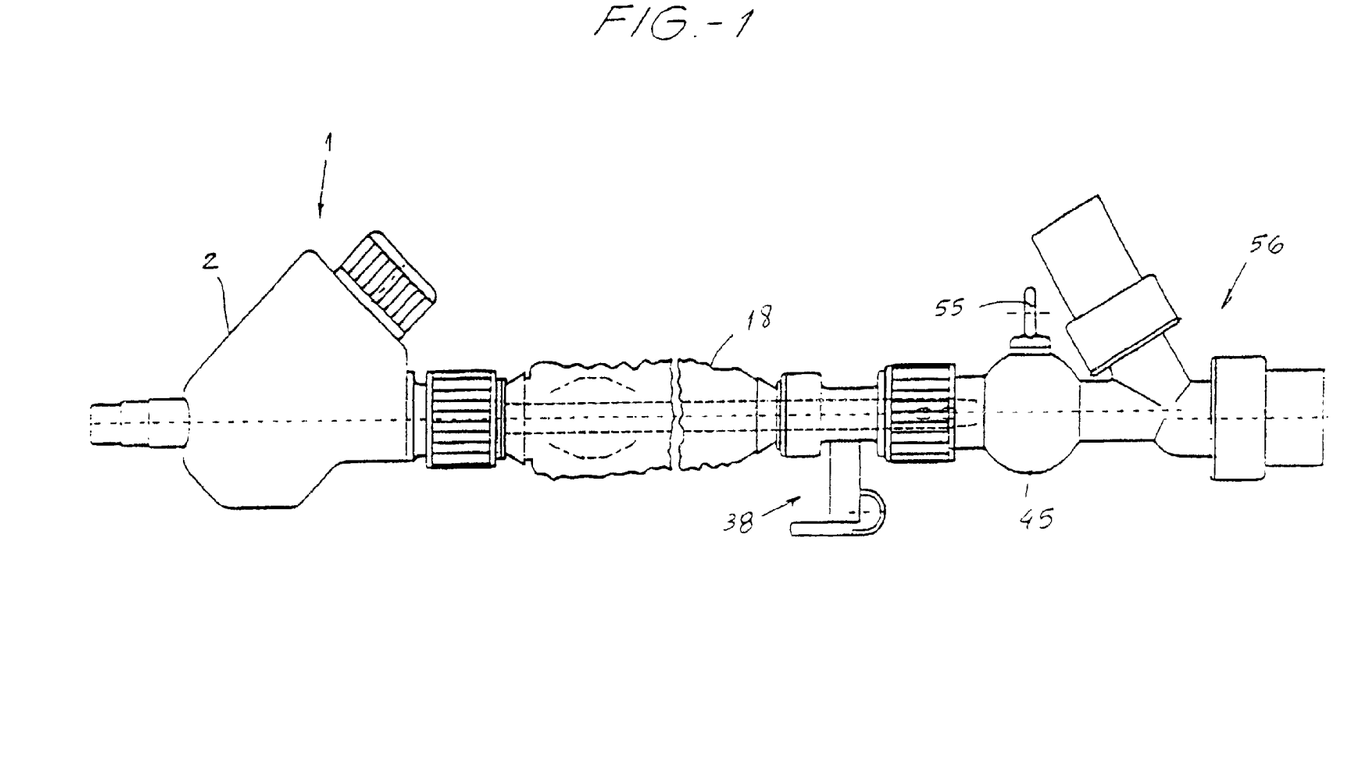
FIG. 1 illustrates an overview of the proposed device.
Figure 2:
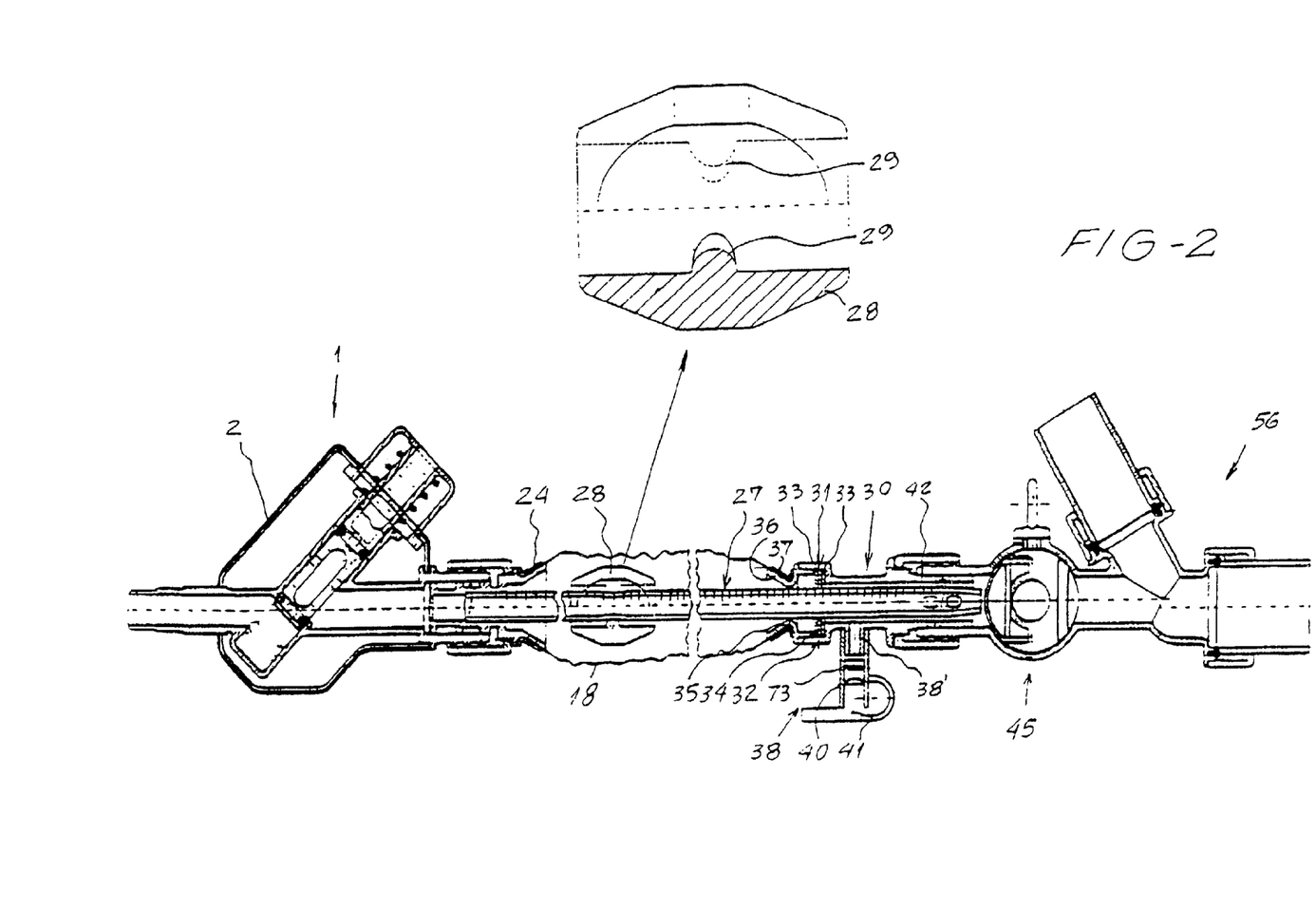
FIG. 2 illustrates an overview of this device, which is showed in cross section, with enlarged detail.

Probe 25, as illustrates FIG. 2, presents a graduation 27, which is representative of its total measure length, being that on said probe 25, is assembled a limiting and marking means 28, that may be dislocated along probe 25, and thus, along graduation 27, allow the operator to pre-determine the course of introduction of same into the patient.

The limiting and marking means 28, as it can be observed in enlarged detail on FIG. 2, is internally provided with a pair of opposed protuberances 29, which act to produce a relative locking effect on the external wall of probe 25. The pair of opposed protuberances 29 thus guarantees if necessary, the application of a determined effort value to produce the dislocation of the limiting and marking means 28 along the probe 25.

Figure 4:
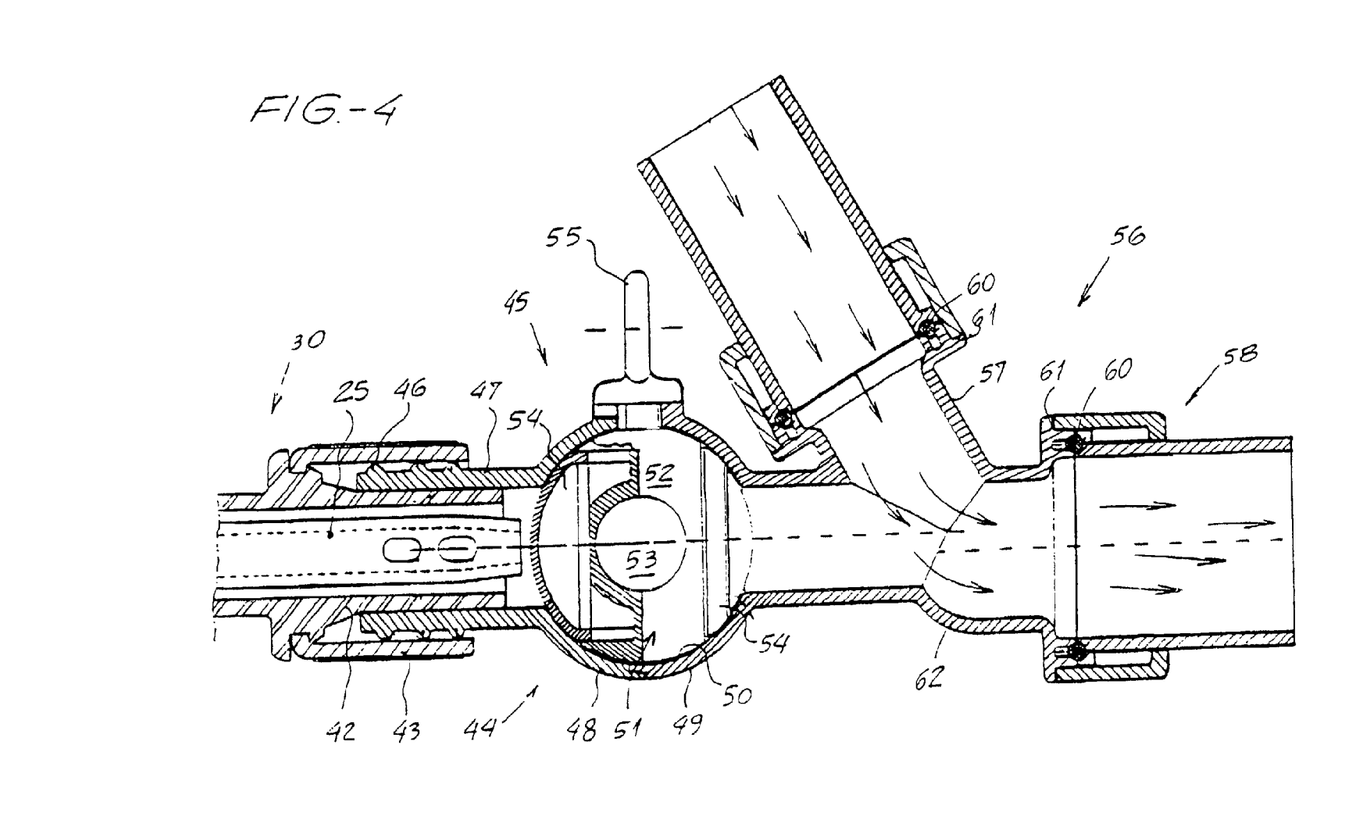
FIG. 4 illustrates a detail in enlarged section, which is taken from FIG. 2, demonstrating the spinning connection for the ventilator and the patient, with a sphere system.
Figure 5:
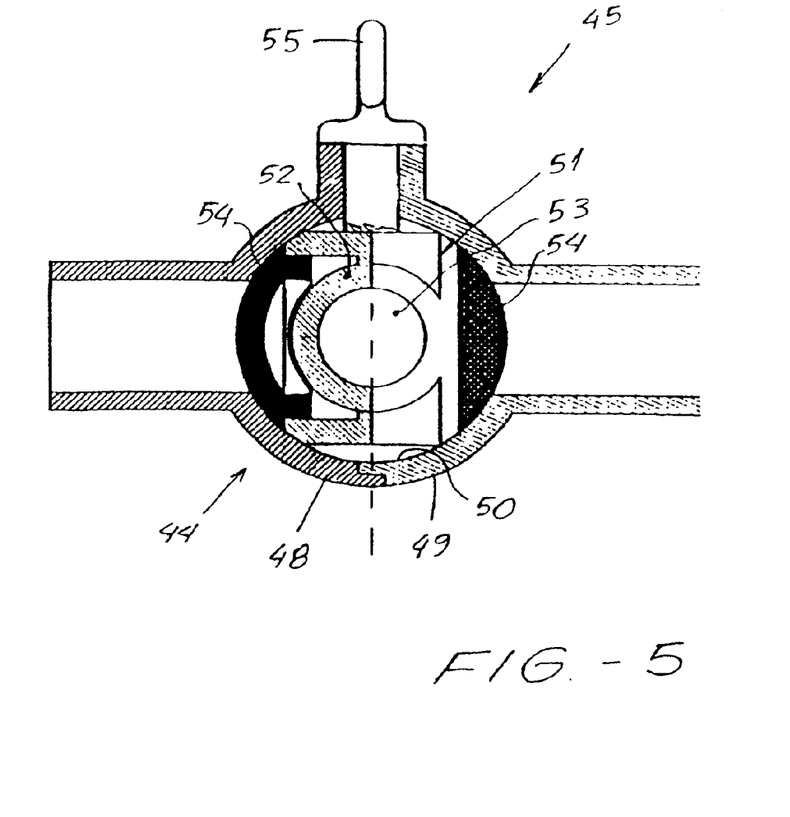
FIG. 5 illustrates a schematic and section view of the sphere shaped selecting key, being the same on its closure condition.

As it can be concluded by the observation of FIGS. 2 and 4, probe 25, crosses frontally, a terminal 30, provided with a casing 31, where a set of sealing rings 32 is assembled, said set being formed by two stiff rings 33, among which is assembled a flexible ring 34.

The casing 31 is closed by a component 35, which adequately presses the ring set 32, and also acts as a fixation place for the plastic sheathing anterior rim 18, being that, for the latter object, it is provided in said component 35, a trunk ending 36, with identical configurations of the other trunk ending 23.

The trunk ending 36 receives a retention ring 37, identical to the other retention ring 24, assembled on the opposed rim of the plastic sheathing 18.

The terminal 30 is provided with an instillation route 38, defined by an radial tubular projection 38', provided with a diaphragm 73, being that said route 38 begins at the wall of terminal 30, and receives the coupling from a tubular sector 40, which incorporates a closing cap 41.

Terminal 30 is provided with a connection 42, which externally receives a tightening element 43, used to produce body 44 coupling with a sphere valve 45.

The tightening element 43 stays on a thread 46, incorporated into a tubular projection 47, provided on sphere valve 45 on body 44.

The sphere valve 45 on body 44 is divided into two portions 48 and 49, each one incorporating half of chamber 50, which covers the sphere shaped element 51, which is formed by a central section 52, provided with a transversal channel 53 and with two supplementary sections 54.

The sphere shaped element 51 is driven by an upper external handle 55, which can be turned along a 90 degree range between two basic positions, which determine whether the transversal channel 53 and sphere valve 45, from valve body 44 longitudinal geometric axis are aligned or not.

The sphere valve 45 isolates the internal environment, where probe 25 is located, allowing or not its passage towards patient/ventilator connection 56.

Sphere valve 45 is provided with a color code which eases its operational condition visualization, i.e., whether open or closed for probe 25 passage, said color code is defined by the fact that central section 52 presents a different coloration from the two additional sections 54. A preferred combination of colors define central section 52 from the sphere shaped element as green, and corresponding additional sections 54 as red. Such a color combination allows visualizing when the sphere valve is open or closed, being that, on its open position, central section 52, as green, stays in alignment with the sphere valve longitudinal geometric axis, on the other hand, on its closed position, the longitudinal sector keeps a transversal positioning regarding the valve body, while the supplementary sections 54 become aligned with the longitudinal geometric axis mentioned above.

The patient/ventilator connection 56 is provided with a shift 57, which receives the connection line that communicates the ventilation equipment (not illustrated), said connection 56 is further provided with another connection 58, which is connected to the patient's coupling tube.

Shift 57 is incorporated so that it presents an inclined angle that causes the maintenance of a non-turbulent laminar air flow, an especially ideal condition, from the point of view of the patient's vital signs.

As it is well illustrated by FIG. 4, the patient/ventilator connection 56 further incorporates sealing rings of the o-rings type, assembled on corresponding terminals 61.

In FIG. 4, it is possible to notice that the air flow provided by the ventilation device does not find any kind of obstacle on its pathway, being that, upon arriving at connection 58, it is provided with a round wall sector 62, which deviates the entrance angle of such flow in a smooth, progressive manner, causing said flow to proceed with no turbulence towards connection 58 longitudinal geometric axis.

Figure 7:
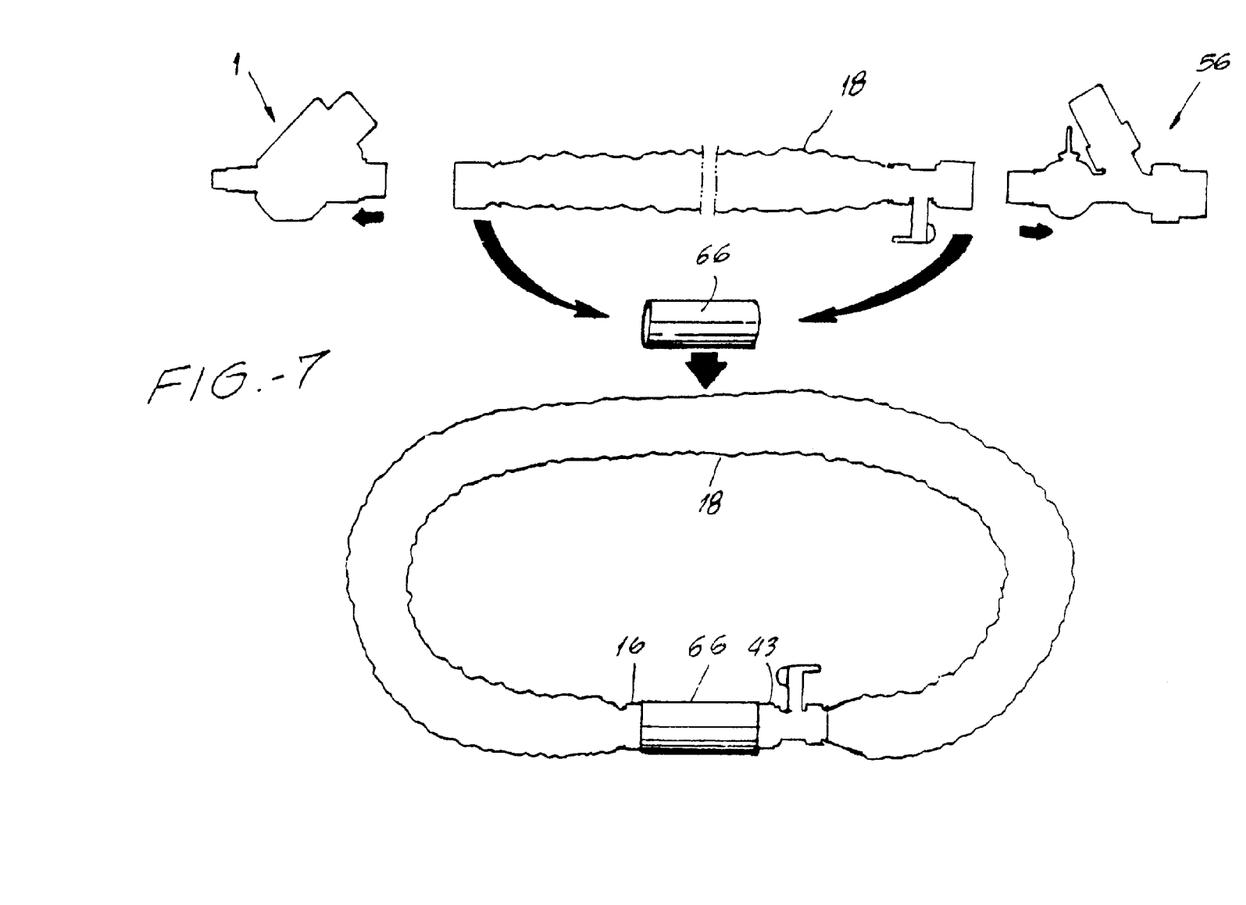
Figure 7A:
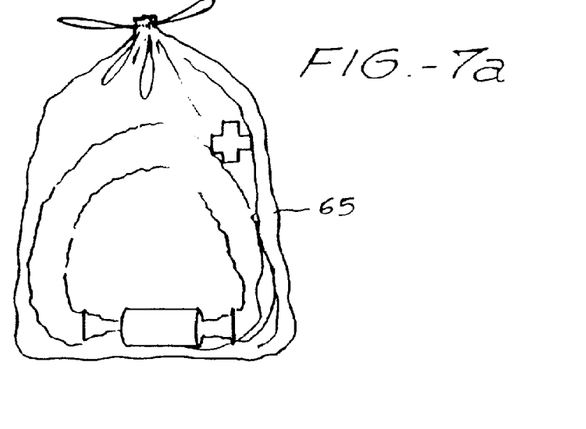
FIG. 7a illustrates a view that represents the sequence following that demonstrated above in FIG. 7, where the refill of such a device is duly prepared for the disposal.

The invention further foresees besides the described device characteristics, the assembling of a set or kit 63, which comprises a package 64 that covers, besides the device unit mentioned, elements that help in its disposal after use, i.e., a plastic sheath 65 and a tube 66, the latter being used to connect both rims of the device refill, as illustrated in FIGS. 7 and 7a.

Figure 6E:
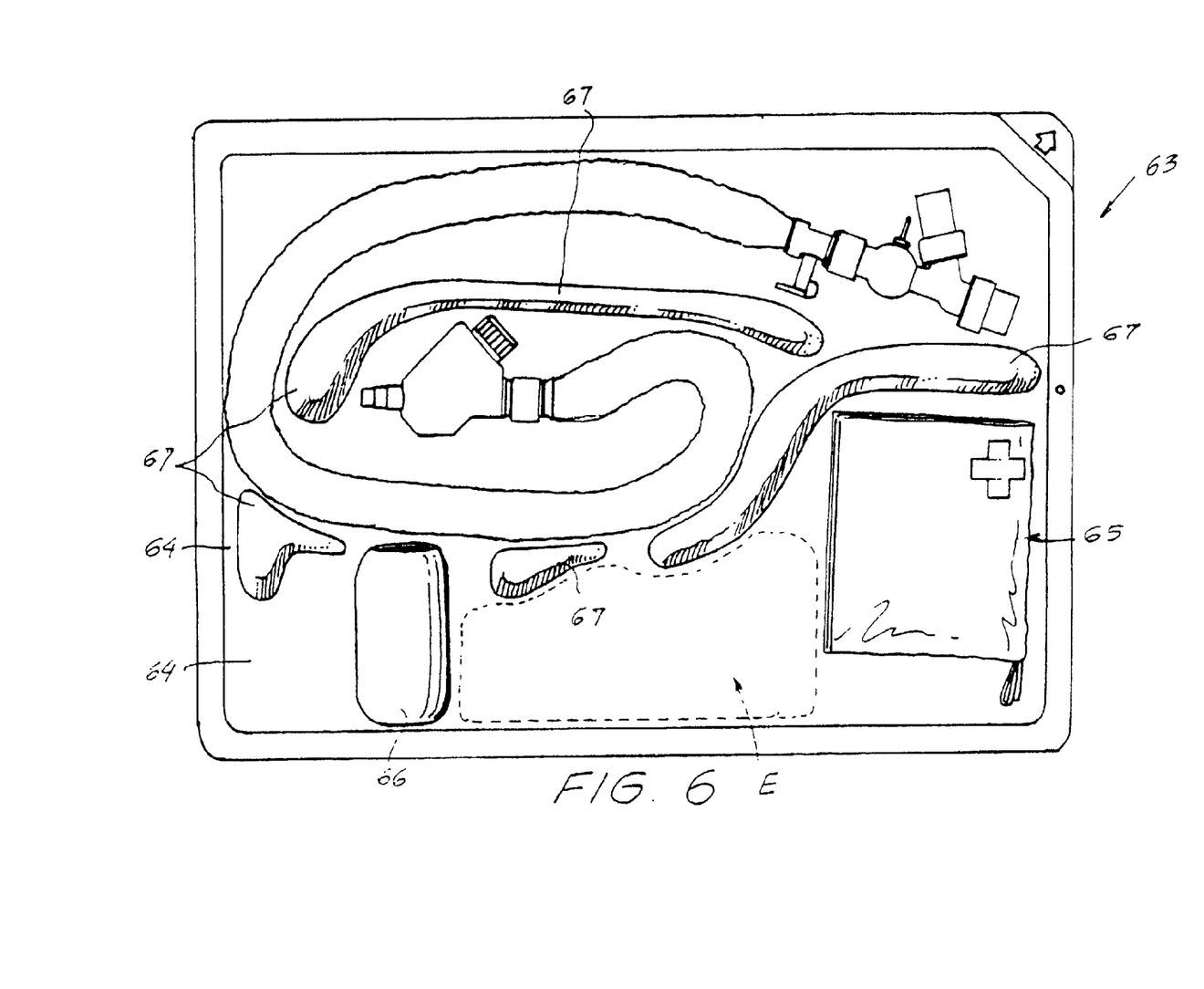
FIG. 6 illustrates a view of the kit set, which comprises the proposed device, along with other components intended to make the safe disposal possible, all of those duly boxed in one package.

Packages 64 presents defined spaces divided by divider walls 67, allowing each covered element to occupy, in a organized manner, a previously studied place, as illustrated on FIG. 6.

Figure 8:
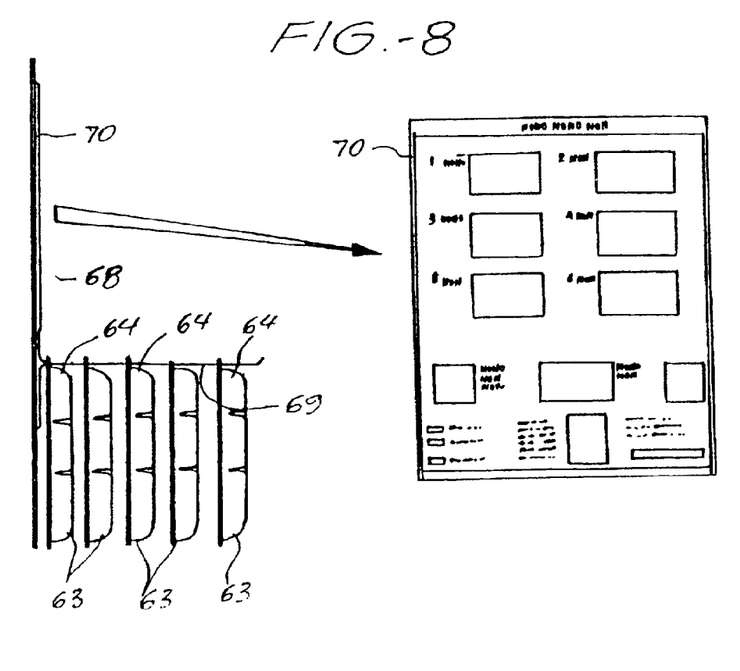
FIG. 8 illustrates a structure where the packaging containing the kit may hereby proposed be positioned in an organized manner.

The proposed kit is also provided with a structure 68, where a determined number of packages 64 can be adequately stored, as demonstrated on FIG. 8.

Structure 68 is provided with one or two parallel horizontal bars 69, that act as a hanger for packages 64, said structure 68 is further provided with a frontal panel 70, schematically illustrated in detail in FIG. 8, where all of the instructions for use of the proposed device are located.

Figure 9:
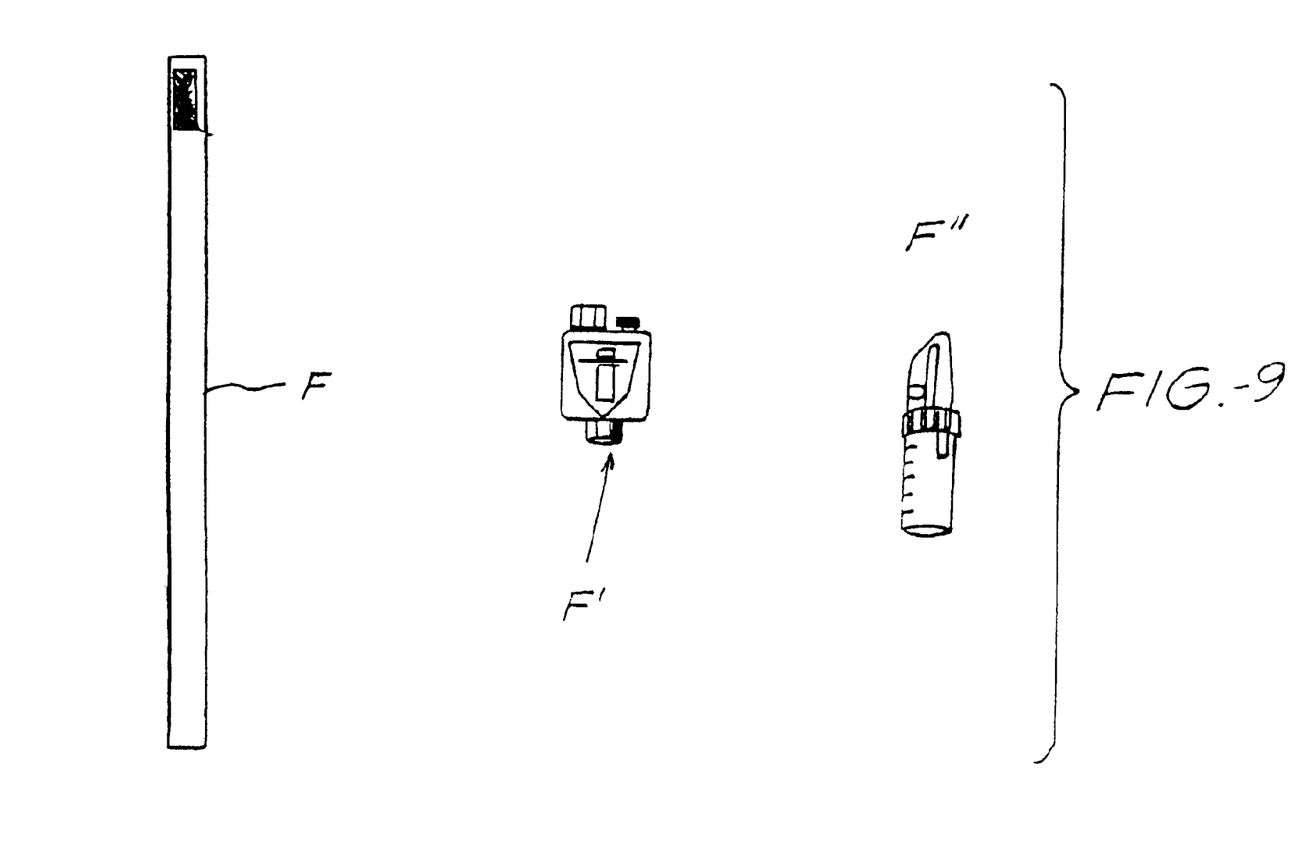
FIG. 9 schematically illustrates three accessories, that separately or jointly, may make up part of the kit, object of this invention.

FIG. 9 illustrates a schematic view of three accessories that individually or jointly may make up part of the proposed kit, said accessories being able to occupy, for instance, the space E, indicated with a dotted line on the packaging, which is specifically demonstrated in FIG. 6.

FIG. 9 accessories comprise an endotracheal tube fixture F, a humidifying filter F' and a secretion collector flask F".

What is claimed is:

1. A secretion suctioning device for an intubated or tracheostomized patient, which comprises:
   (a) a suctioning valve comprising:
      (i) a main body defining an elongated internal chamber therein;
      (ii) a hollow connection having a first end disposed outside the main body, and a second end disposed inside the main body and communicating with the internal chamber;
      (iii) an internal channel having a first end communicating with the internal chamber, and a second end;
      (iv) an on/off button;
      (v) a selecting obstruction device disposed in the internal chamber and having an upper end attached to the on/off button, a lower end, and a passage opening therebetween, and wherein the selecting obstruction device is operable to be moved reversibly from a first position where the passage opening provides a communication between the connection and the internal channel to a second position where the selecting obstruction device blocks the communication between the connection and the internal channel; and
      (iv) a rim connector attached to the second end of the internal channel and disposed outside the main body;
   (b) a hollow interconnection component having a first end releasably attached to the rim connector, and a second end;
   (c) a hollow terminal having a first end, and a second end;
   (d) a hollow, elongated probe having a first end received within an inside wall of the interconnection component, and a second end slidably received within the terminal;
   (e) a sheathing for the probe and having a first end attached to the second end of the interconnection component, and a second end attached to the first end of the terminal;
   (f) a sphere valve having a first end releasably attached to the second end of the terminal, and a second end; and
   (g) a hollow patient/ventilator connection attached to the second end of the sphere valve.

2. The device of claim 1, wherein the suctioning valve may be conveniently locked.

3. The device of claim 1, wherein the first end of the connection of the suctioning valve has a progressive staggering for receiving vacuum lines of varied diameters.

4. The device of claim 1, wherein the probe has a sleeve shaped tie rod.

5. The device of claim 1, wherein the probe has a graduation, and a marker is slidably mounted on the probe.

6. The device of claim 5, wherein the marker has a pair of opposed protuberances that engage the probe and provide a locking force.

7. The device of claim 1, wherein the terminal has an instillation route defined by a tubular projection radially extending from the terminal.

8. The device of claim 7, where the tubular projection has a diaphragm.

9. The device of claim 7, wherein the sphere valve has a casing, a sphere shaped element disposed in the casing and comprising a central section and two supplementary sections, and a handle connected to the central section, the central section having a transversal channel sized to receive the probe, and wherein the handle is operable to be turned reversibly from a first position where the transversal channel is aligned with the probe to open a passage for the probe toward the patient/ventilator connection to a second position where the transversal channel is not aligned with the probe to close the passage.

10. The device of claim 9, wherein the sphere valve has a color combination indicate whether the sphere valve opens or closes the passage.

11. The device of claim 10, wherein the central section has a color that is different from that of the two supplementary sections.

12. The device of claim 11, wherein the central section is in green color, and the supplementary sections are in red color.

13. The device of claim 9, wherein the patient/ventilator connection has a hollow shift having a first end for communicating with a ventilating equipment to receive an air flow therefrom, and a second end, and wherein the patient/ventilator connection further has a connector attached to the second end of the hollow shift for receiving a patient's coupling tube.

14. The device of claim 13, wherein the hollow shift is disposed in an inclination angle with respect to the patient's coupling tube to help maintain the air flow in a non turbulent laminar manner.

15. The device of claim 14, wherein the patient/ventilator connection has a round wall sector for directing the air flow in a smooth and progressive manner.

16. The device of claim 13, wherein each of the first end of the hollow shift and the connector of the patient/ventilator connection has a sealing of o-ring.

17. The device of claim 1, wherein the suctioning valve is of an anatomic and inclined shape.

18. The device of claim 1, wherein the first end of the interconnection component has at least one external sealing ring, and said first end of the interconnection component is received within an inside wall of the rim connector with at least one said external sealing ring in contact with the inside wall.

19. The device of claim 18, wherein the second end of the interconnection component has a trunk-shaped configuration, and the first end of the sheathing is placed around the trunk shaped configuration and releasably attached to the trunk shaped configuration by a first retention member.

20. The device of claim 19, wherein the interconnection component further has a median portion between the first end and second end, and the rim connector has an external thread, and wherein the device further has a first binding element which is operable to engage the median portion of the interconnection component and to be threaded onto the rim connector.

21. The device of claim 1, wherein the first end of the terminal has at least one external sealing ring, and the device further has a second binding element which has a trunk shaped end and is operable to engage at least one said external sealing ring of the first end of the terminal, and wherein the second end of the sheathing is placed around the trunk shaped end of the second binding element and releasably attached to the trunk shaped configuration by a second retention member.

22. The device of claim 1, wherein the second end of the terminal is received within an inside wall of the first end of the sphere valve, and the first end of the sphere valve has an external thread, and wherein the device further has a third binding element which is operable to engage the terminal and to be threaded onto the first end of the sphere valve.

* * * * *